United States Patent
Tegg et al.

(10) Patent No.: US 11,890,044 B2
(45) Date of Patent: Feb. 6, 2024

(54) PULMONARY VEIN ISOLATION BALLOON CATHETER

(71) Applicant: ST. JUDE MEDICAL, CARDIOLOGY DIVISION, INC., St. Paul, MN (US)

(72) Inventors: Troy T. Tegg, Elk River, MN (US); Salo Arias, Brooklyn Park, MN (US); Derek Sutermeister, Ham Lake, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 791 days.

(21) Appl. No.: 16/467,343

(22) PCT Filed: Dec. 5, 2017

(86) PCT No.: PCT/US2017/064713
§ 371 (c)(1),
(2) Date: Jun. 6, 2019

(87) PCT Pub. No.: WO2018/106688
PCT Pub. Date: Jun. 14, 2018

(65) Prior Publication Data
US 2020/0085484 A1 Mar. 19, 2020

Related U.S. Application Data

(60) Provisional application No. 62/578,352, filed on Oct. 27, 2017, provisional application No. 62/432,065, filed on Dec. 9, 2016.

(51) Int. Cl.
*A61B 18/14* (2006.01)
*A61B 18/02* (2006.01)
(Continued)

(52) U.S. Cl.
CPC .......... *A61B 18/02* (2013.01); *A61B 18/1492* (2013.01); *A61B 2018/00166* (2013.01);
(Continued)

(58) Field of Classification Search
CPC .............. A61B 18/02; A61B 2090/064; A61B 2090/065; A61B 18/1492;
(Continued)

(56) References Cited

U.S. PATENT DOCUMENTS 3,333,434 A * 8/1967 Jacques ...................... F25J 3/04
62/646
4,650,463 A 3/1987 Leveen et al.
(Continued)

FOREIGN PATENT DOCUMENTS

CN 202537649 U 11/2012
EP 3120792 A1 1/2017
(Continued)

*Primary Examiner* — Linda C Dvorak
*Assistant Examiner* — Ryan T Clark
(74) *Attorney, Agent, or Firm* — Armstrong Teasdale LLP

(57) ABSTRACT

The instant disclosure relates to electrophysiology catheters for tissue ablation. In particular, the instant disclosure relates to a cryogenic ablation balloon with safety features that facilitate identification of a leak into an interstitial space between inner and outer balloons as part of the ablation balloon catheter assembly, and prevents egress of cryogenic fluid out of the ablation balloon.

19 Claims, 10 Drawing Sheets

(51) Int. Cl.
  *A61B 90/00* (2016.01)
  *A61B 18/00* (2006.01)
  *A61M 25/01* (2006.01)

(52) U.S. Cl.
  CPC ........... *A61B 2018/00255* (2013.01); *A61B 2018/00351* (2013.01); *A61B 2018/00375* (2013.01); *A61B 2018/00577* (2013.01); *A61B 2018/00791* (2013.01); *A61B 2018/00946* (2013.01); *A61B 2018/00994* (2013.01); *A61B 2018/0212* (2013.01); *A61B 2018/0262* (2013.01); *A61B 2090/064* (2016.02); *A61B 2090/065* (2016.02); *A61B 2218/002* (2013.01); *A61B 2218/007* (2013.01); *A61M 25/0116* (2013.01); *A61M 25/0127* (2013.01); *A61M 25/0136* (2013.01)

(58) Field of Classification Search
  CPC A61B 2018/00166; A61B 2018/00255; A61B 2018/00351; A61B 2018/00375; A61B 2018/00577; A61B 2018/00791; A61B 2018/00946; A61B 2018/00994; A61B 2018/0212; A61B 2018/0262; A61B 2218/002; A61B 2218/007; A61M 25/0116; A61M 25/0127; A61M 25/0136
  See application file for complete search history.

(56) References Cited

U.S. PATENT DOCUMENTS

| | | | | |
|---|---|---|---|---|
| 4,676,258 | A * | 6/1987 | Inokuchi | A61N 1/403 607/154 |
| 4,709,698 | A * | 12/1987 | Johnston | A61B 18/08 606/41 |
| 5,106,360 | A * | 4/1992 | Ishiwara | A61N 5/1002 600/3 |
| 5,345,936 | A * | 9/1994 | Pomeranz | A61B 5/6853 600/374 |
| 5,397,307 | A * | 3/1995 | Goodin | A61M 25/10 604/103.08 |
| 5,514,091 | A * | 5/1996 | Yoon | A61F 13/38 600/207 |
| 5,549,555 | A * | 8/1996 | Sohn | A61M 25/1002 604/101.01 |
| 5,624,392 | A * | 4/1997 | Saab | A61M 25/1029 604/113 |
| 5,645,529 | A * | 7/1997 | Fagan | A61M 25/1011 604/101.01 |
| 5,758,505 | A * | 6/1998 | Dobak, III | A61B 18/02 606/23 |
| 6,068,638 | A * | 5/2000 | Makower | A61B 17/11 606/159 |
| 6,164,283 | A | 12/2000 | Lesh | |
| 6,235,019 | B1 | 5/2001 | Lehmann et al. | |
| 6,355,031 | B1 * | 3/2002 | Edwards | A61B 18/12 606/41 |
| 6,491,710 | B2 | 10/2002 | Satake | |
| 6,502,576 | B1 | 1/2003 | Lesh | |
| 6,514,245 | B1 * | 2/2003 | Williams | A61F 7/12 128/898 |
| 6,575,933 | B1 * | 6/2003 | Wittenberger | A61B 18/02 128/898 |
| 6,575,966 | B2 * | 6/2003 | Lane | A61B 18/02 606/7 |
| 6,652,515 | B1 | 11/2003 | Maguire et al. | |
| 6,866,662 | B2 | 3/2005 | Fuimaono et al. | |
| 6,905,494 | B2 * | 6/2005 | Yon | A61B 18/02 606/20 |
| 7,371,231 | B2 * | 5/2008 | Rioux | A61B 18/1492 606/32 |
| 7,442,190 | B2 | 10/2008 | Abboud et al. | |
| 7,527,622 | B2 * | 5/2009 | Lane | A61B 18/02 604/101.01 |
| 7,736,360 | B2 | 6/2010 | Mody et al. | |
| 8,380,299 | B2 * | 2/2013 | LePivert | A61B 18/02 604/21 |
| 8,382,746 | B2 * | 2/2013 | Williams | A61M 25/1034 606/21 |
| 8,568,399 | B2 * | 10/2013 | Azamian | A61B 18/24 606/41 |
| 8,728,073 | B2 | 5/2014 | McDaniel | |
| 8,790,300 | B2 | 7/2014 | Tun et al. | |
| 9,393,070 | B2 * | 7/2016 | Gelfand | A61B 18/18 |
| 9,414,878 | B1 | 8/2016 | Wu et al. | |
| 9,579,448 | B2 | 2/2017 | Chow et al. | |
| 9,636,172 | B2 * | 5/2017 | Hu | A61B 18/02 |
| 2002/0010460 | A1 * | 1/2002 | Joye | A61B 18/02 606/23 |
| 2002/0019627 | A1 | 2/2002 | Maguire et al. | |
| 2002/0022833 | A1 * | 2/2002 | Maguire | A61B 17/2202 606/41 |
| 2002/0045892 | A1 * | 4/2002 | Kramer | A61B 18/02 607/113 |
| 2002/0077625 | A1 | 6/2002 | Lev | |
| 2002/0151924 | A1 * | 10/2002 | Shiber | A61B 8/12 606/194 |
| 2003/0036752 | A1 * | 2/2003 | Joye | A61B 18/02 606/21 |
| 2005/0228367 | A1 | 10/2005 | Abboud et al. | |
| 2005/0273095 | A1 | 12/2005 | Taimisto et al. | |
| 2006/0030814 | A1 * | 2/2006 | Valencia | A61M 25/00 604/93.01 |
| 2006/0089637 | A1 | 4/2006 | Werneth et al. | |
| 2007/0142830 | A1 * | 6/2007 | DiCarlo | A61B 18/1477 606/41 |
| 2008/0171974 | A1 | 7/2008 | LaFontaine et al. | |
| 2008/0177228 | A1 * | 7/2008 | Burton | A61M 25/10 425/523 |
| 2009/0157066 | A1 | 6/2009 | Satake | |
| 2009/0234345 | A1 | 9/2009 | Hon | |
| 2009/0287203 | A1 | 11/2009 | Mazzone et al. | |
| 2009/0299356 | A1 * | 12/2009 | Watson | A61M 25/1006 606/21 |
| 2010/0100087 | A1 | 4/2010 | Mazzone et al. | |
| 2011/0190751 | A1 | 8/2011 | Ingle et al. | |
| 2011/0301584 | A1 * | 12/2011 | Beck | A61B 18/22 606/15 |
| 2012/0029509 | A1 * | 2/2012 | Smith | A61B 18/1492 606/41 |
| 2012/0172680 | A1 | 7/2012 | Gelfand et al. | |
| 2012/0197245 | A1 | 8/2012 | Burnett et al. | |
| 2014/0046252 | A1 | 2/2014 | Boatman | |
| 2014/0058369 | A1 | 2/2014 | Hon | |
| 2014/0180248 | A1 * | 6/2014 | Salik | A61B 18/00 604/509 |
| 2014/0207131 | A1 | 7/2014 | Harmouche et al. | |
| 2014/0303730 | A1 * | 10/2014 | McGuire | A61B 17/8811 623/17.12 |
| 2014/0358137 | A1 | 12/2014 | Hu | |
| 2014/0371736 | A1 | 12/2014 | Levin et al. | |
| 2014/0378966 | A1 | 12/2014 | Haverkost et al. | |
| 2015/0126985 | A1 * | 5/2015 | Newell | A61B 18/02 606/21 |
| 2015/0133772 | A1 * | 5/2015 | Miesse | A61B 1/00165 604/8 |
| 2015/0141982 | A1 * | 5/2015 | Lee | A61B 5/6853 606/41 |
| 2015/0148791 | A1 * | 5/2015 | Birdsall | A61B 18/02 606/21 |
| 2015/0157382 | A1 | 6/2015 | Avitall et al. | |
| 2015/0216581 | A1 | 8/2015 | Duong et al. | |
| 2015/0265329 | A1 | 9/2015 | Lalonde et al. | |
| 2015/0313732 | A1 * | 11/2015 | Fulton, III | A61F 2/82 623/1.11 |
| 2016/0220294 | A1 | 8/2016 | Babkin et al. | |
| 2016/0324571 | A1 | 11/2016 | Beeckler et al. | |

(56) References Cited

U.S. PATENT DOCUMENTS

2017/0135778 A1* 5/2017 Gill .................... A61B 17/3417
2020/0405336 A1* 12/2020 Martin ............. A61B 17/22012
2021/0260340 A1* 8/2021 Soltis .................. A61M 25/005

FOREIGN PATENT DOCUMENTS

WO      2014113864  A1     7/2014
WO      2014189997  A2     11/2014

* cited by examiner

A-A

B-B

PULMONARY VEIN ISOLATION BALLOON CATHETER

CROSS-REFERENCE TO RELATED APPLICATIONS

This application claims the benefit of United States provisional application Nos. 62/578,352, filed 27 Oct. 2017; and 62/432,065, filed 9 Dec. 2016, both of which are hereby incorporated by reference in their entirety as though fully set forth herein.

BACKGROUND a. Field

The instant disclosure relates to catheters, in particular catheters for conducting ablation therapy within a heart. In one embodiment, the instant disclosure relates to a catheter for treating cardiac arrhythmias by ablating in the vicinity of pulmonary venous tissue using a balloon filled with cryogenic fluid.

b. Background Art

The human heart routinely experiences electrical impulses traversing its many surfaces and ventricles, including the endocardial chamber. As part of each heart contraction, the heart depolarizes and repolarizes, as electrical currents spread across the heart and throughout the body. In healthy hearts, the surfaces and ventricles of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of synchronous atrioventricular contractions, and blood flow stasis. All of these conditions have been associated with a variety of ailments, including death.

Catheters are used in a variety of diagnostic and/or therapeutic medical procedures to correct conditions such as atrial arrhythmia, including for example, ectopic atrial tachycardia, atrial fibrillation, and atrial flutter.

Typically in a procedure, a catheter is manipulated through a patient's vasculature to, for example, a patient's heart, and carries one or more electrodes which may be used for mapping, ablation, diagnosis, or other treatments. Where an ablation therapy is desired to alleviate symptoms including atrial arrhythmia, an ablation catheter imparts ablative energy to cardiac tissue to create a lesion in the cardiac tissue. The lesioned tissue is less capable of conducting electrical impulses, thereby disrupting undesirable electrical pathways and limiting or preventing stray electrical impulses that lead to arrhythmias. The ablation catheter may utilize ablative energy including, for example, radio frequency (RF), cryoablation, laser, chemical, and high-intensity focused ultrasound. As readily apparent, such an ablation treatment requires precise positioning of the ablation catheter for optimal results.

Typically, ablation therapies have been delivered by making a number of individual ablations in a controlled fashion in order to form a lesion line. Such lesion lines are often desirable around/between the pulmonary veins in the left atrium of the heart which have been associated with the introduction of erratic electric impulses into the heart. There are devices in development or being commercialized that attempt to achieve a sufficient lesion line with minimal applications of energy. Existing designs range from diagnostic catheters with a hoop and balloon mounted designs with energy applying or extracting features. The existing designs often suffer from a lack of continuous contact around a circumference of the pulmonary vein during therapy delivery, resulting in inconsistent lesion lines and incomplete electrical impulse blockage.

The foregoing discussion is intended only to illustrate the present field and should not be taken as a disavowal of claim scope.

BRIEF SUMMARY

The instant disclosure relates to electrophysiology catheters for tissue ablation within a cardiac muscle. In particular, the instant disclosure relates to an electrophysiology catheter including a dual-layer ablation balloon that contains a cryogenic fluid for administering an ablation therapy on a pulmonary vein.

Aspects of the present disclosure are directed to an ablation catheter system including a catheter shaft including proximal and distal ends, dual cryogenic ablation balloons coupled to the distal end of the catheter shaft, an interstitial space between the inner and outer balloons, a manifold, and a first and second lumen in fluid communication with the interstitial space. The dual cryogenic ablation balloons include inner and outer balloons. The interstitial space captures cryogenic fluid that escapes from an internal cavity of the inner balloon. The manifold delivers cryogenic fluid to the internal cavity of the inner balloon. In some more specific embodiments, the first lumen is a vacuum lumen that draws a vacuum within the interstitial space and further draws captured cryogenic fluid out of the interstitial space and into the vacuum lumen.

Various embodiments of the present disclosure are directed to a dual-layer ablation balloon that includes an inner balloon including an internal cavity, an outer balloon that encapsulated the inner balloon, an interstitial space between the inner and outer balloons, and a spacer coupled between proximal portions of the inner and outer balloons. The internal cavity of the inner balloon receives a cryogenic fluid in a liquid state and facilitates a state transfer of the cryogenic fluid into a gaseous state. The spacer maintains the interstitial space between the inner and outer balloons in response to a vacuum pressure within the interstitial space. In some specific embodiments, the interstitial space is configured and arranged to capture cryogenic fluid that escapes from the internal cavity of the inner balloon.

Some embodiments of the present disclosure are directed to a dual-layer ablation balloon including an inner balloon including an internal cavity, an outer balloon that encapsulates the inner balloon, an interstitial space between the inner and outer balloons, and an adaptor that mechanically couples the inner and outer balloons to a catheter shaft, and radially and longitudinally offsets proximal portions of the inner and outer balloons. The internal cavity of the inner balloon receives a cryogenic fluid in a liquid state and facilitates a state transfer of the cryogenic fluid into a gaseous state. In specific embodiments, the dual-layer ablation balloon further includes a first lumen in fluid communication with the interstitial space. The first lumen draws a vacuum within the interstitial space and further draws captured cryogenic fluid out of the interstitial space and into the vacuum lumen.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1A:
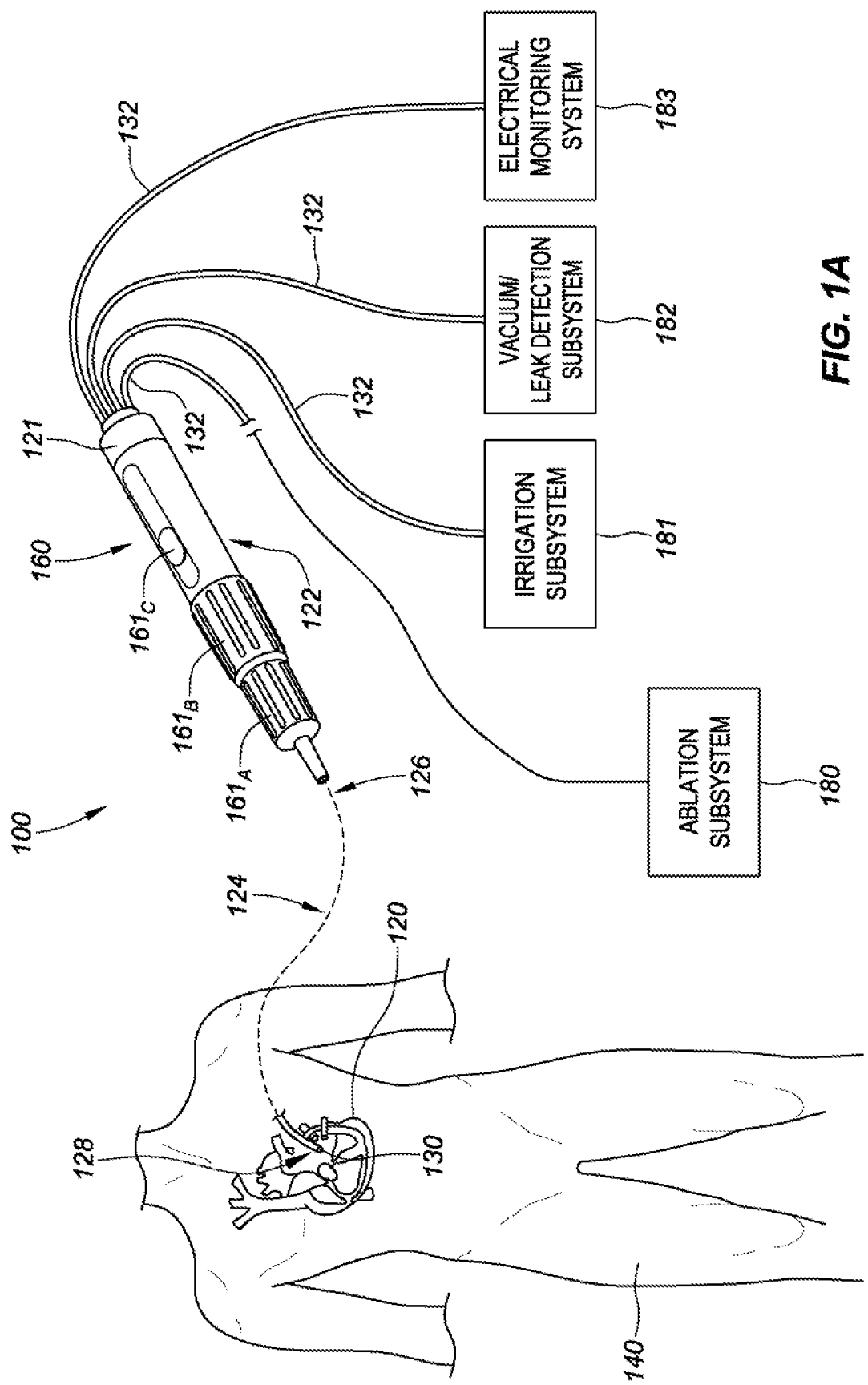
FIG. 1A is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for tissue ablation within a cardiac muscle. In particular, the instant disclosure relates to an electrophysiology catheter including a dual-layer ablation balloon that contains a cryogenic fluid for administering an ablation therapy on a pulmonary vein. Details of the various embodiments of the present disclosure are described below with specific reference to the figures.

Referring now to the drawings wherein like reference numerals are used to identify similar components in the various views, FIG. 1A is a schematic and diagrammatic view of a catheter ablation system 100 for performing tissue ablation procedures. In an exemplary embodiment, tissue 120 comprises cardiac tissue (e.g., myocardial tissue) within a human body 140. It should be understood, however, that the system may find application in connection with a variety of other tissue within human and non-human bodies, and therefore, the present disclosure is not meant to be limited to the use of the system in connection with only cardiac tissue and/or human bodies.

Catheter ablation system 100 may include a catheter 160 and an ablation subsystem 180 for controlling an ablation therapy conducted by an ablation balloon 130 at a distal end 128 of the catheter 160. The ablation subsystem 100 may control the generation and/or application of ablative energy including, in the present embodiment, cryoablation.

In the exemplary embodiment of FIG. 1A, catheter 160 is provided for examination, diagnosis, and/or treatment of internal body tissue such as myocardial tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end 128 of the catheter shaft 124.

In an exemplary embodiment, ablation balloon 130 is manipulated through vasculature of a patient 140 using handle 122 to steer one or more portions of shaft 124 and position the ablation balloon at a desired location within tissue 120 (e.g., a cardiac muscle). In the present embodiment, the ablation balloon includes one or more cryoablation manifolds that, when operated by ablation subsystem 180, ablates the tissue in contact with the ablation balloon (and in some cases tissue in proximity to the ablation balloon may be ablated by thermal transfer through the blood pool and to the proximal tissue).

In various specific embodiments of the present disclosure, catheter 160 may include electrophysiology electrodes and one or more positioning sensors (e.g., ring electrodes or magnetic sensors) at a distal end 128 of catheter shaft 124. In such an embodiment, the electrophysiology electrodes acquire electrophysiology data relating to cardiac tissue 120 in contact with the electrodes, while the positioning sensor(s) generate positioning data indicative of the 3-D position of the ablation balloon 130 within patient 140. In further embodiments, the catheter 160 may further include other conventional catheter components such as, for example and without limitation, steering wires and actuators, irrigation lumens and ports, pressure sensors, contact sensors, temperature sensors, additional electrodes, and corresponding conductors or leads.

Connector 121 provides mechanical and electrical connection(s) for one or more cables 132 extending, for example, from ablation subsystem 180 (through catheter handle 122 and shaft 124) to ablation balloon 130 mounted on a distal end 128 of the catheter shaft 124. The connector 121 may also provide mechanical, electrical, and/or fluid connections for cables 132 extending from other components in catheter system 100, such as, for example, irrigation subsystem 181 (when the catheter 160 is an irrigated catheter), vacuum/leak detection subsystem 182, and an electrical monitoring system 183. The vacuum/leak detection subsystem 182 may be used to both draw spent cryogenic gas from the ablation balloon 130, and to determine whether a leak has developed in an interstitial space between a dual layer balloon (as discussed in more detail in reference to FIGS. 5-5C). The connector 121 is conventional in the art and is disposed at a proximal end of the catheter handle 122.

Handle 122 provides a location for a clinician to hold catheter 160, and may further provide steering or guidance for the shaft 124 within patient's body 140. For example, in the present embodiment, the handle includes two actuators $161_{A-B}$ which facilitate manipulation of a distal end 128 of the shaft to steer the shaft in two perpendicularly extending planes. The handle 122 also includes a slider $161_C$ which facilitates longitudinal manipulation of an inner shaft relative to an outer shaft (as discussed in more detail in reference to FIG. 1B). In other embodiments, control of the catheter may be automated by robotically driving or controlling the catheter shaft, or driving and controlling the catheter shaft using a magnetic-based (and/or impedance-based) guidance system.

Catheter shaft 124 is an elongated, tubular, and flexible member configured for movement within a patient's body 140. The shaft supports an ablation balloon 130 at a distal end 128 of catheter 160. The shaft may also permit transport, delivery and/or removal of fluids (including irrigation fluids, cryogenic fluids, and body fluids), medicines, and/or surgical tools or instruments. The shaft, which may be made from conventional materials used for catheters, such as polyurethane, defines one or more lumens configured to house and/or transport electrical conductors, fluids, and/or surgical tools. The catheter may be introduced into a blood vessel or other structure within the body through a conventional introducer sheath.

In an exemplary cardiac ablation therapy, to correct for atrial arrhythmia, the introducer sheath is introduced through a peripheral vein (typically a femoral vein) and advanced into the right atrium. In what is referred to as a transseptal approach, the introducer sheath then makes an incision in the fossa ovalis (the tissue wall between the left and right atriums), extends through the incision in the fossa ovalis, and may be anchored thereto. The ablation catheter may then be extended through a lumen of the introducer sheath into the left atrium. Catheter shaft 124 of ablation catheter 160 may then be steered, or otherwise guided (e.g., via guidewire which extends through a guidewire lumen that extends through a length of the ablation catheter), through the left atrium to position an ablation balloon 130 into a desired location within the left atrium (e.g., a pulmonary vein).

During cardiac ablation therapy, it is desirable to align the longitudinal axis of ablation balloon 130 with a centerline of a target pulmonary vein at which the ablation therapy is to take place. Proper alignment may be particularly difficult, in many embodiments, due to the transseptal approach through the fossa ovalis which causes catheter shaft 124 to be biased toward a right-side of a patient's body 140. This bias places an additional torque on ablation catheter system 100, which may result in the ablation balloon 130, after alignment with the pulmonary vein, to bias away from the centerline of the pulmonary vein. Where the ablation balloon is deployed and extended into contact with the pulmonary vein, but off-axis from the pulmonary vein, the ablation balloon may unevenly contact the pulmonary vein resulting in non-circumferential ablation of the pulmonary vein tissue.

Various embodiments of the present disclosure are directed to ablation therapy of one or more pulmonary veins via cryoablation. To achieve the desired cooling within the ablation balloon 130, cryogenic fluid (also referred to as cryofluid) delivered to the balloon must sufficiently expand within the balloon to phase change from a liquid to a gas. The phase change of the cryofluid requires a large amount of energy which has a cooling effect in proximity to the phase change. As the cryofluid expands to its gaseous state, the pressure within the balloon increases. Aspects of the present disclosure are directed to controlling the pressure within the ablation balloon 130. Further, aspects of the present disclosure are directed to safety features intended to prevent and/or sense a cryogenic fluid leak. For example, embodiments of the present disclosure are directed to a dual-layer balloon with an interstitial space therebetween. Where the inner balloon ruptures (or otherwise leaks cryogenic fluid), the outer balloon contains the cryogenic fluid to prevent a leak of cryofluid into the cardiovascular system of the patient. Where a leak of cryogenic fluid into the interstitial space occurs, a vacuum source which may be fluidly coupled to the interstitial space via a lumen extending a length of the catheter shaft 124 will experience a reduced vacuum state. A vacuum/leak detection subsystem 182 (including the vacuum source) will receive a signal indicative of the reduced vacuum state and take corrective action. For example, the vacuum/leak detection subsystem 182 may abort the ablation therapy by shutting one or more valves or delivery paths that deliver the cryofluid to the balloon 130. In more specific embodiments, other actions may be taken to quickly alleviate pressure within the balloon; for example, dumping the head pressure and/or exhaust pressure.

Aspects of the present disclosure improve the efficacy of the various ablation balloon safety features by reducing pressure sensing lag times, allowing for more timely preventative measures in response to a leak/rupture event of the inner balloon-reducing the likelihood of a dual-balloon failure.

Figure 1B:
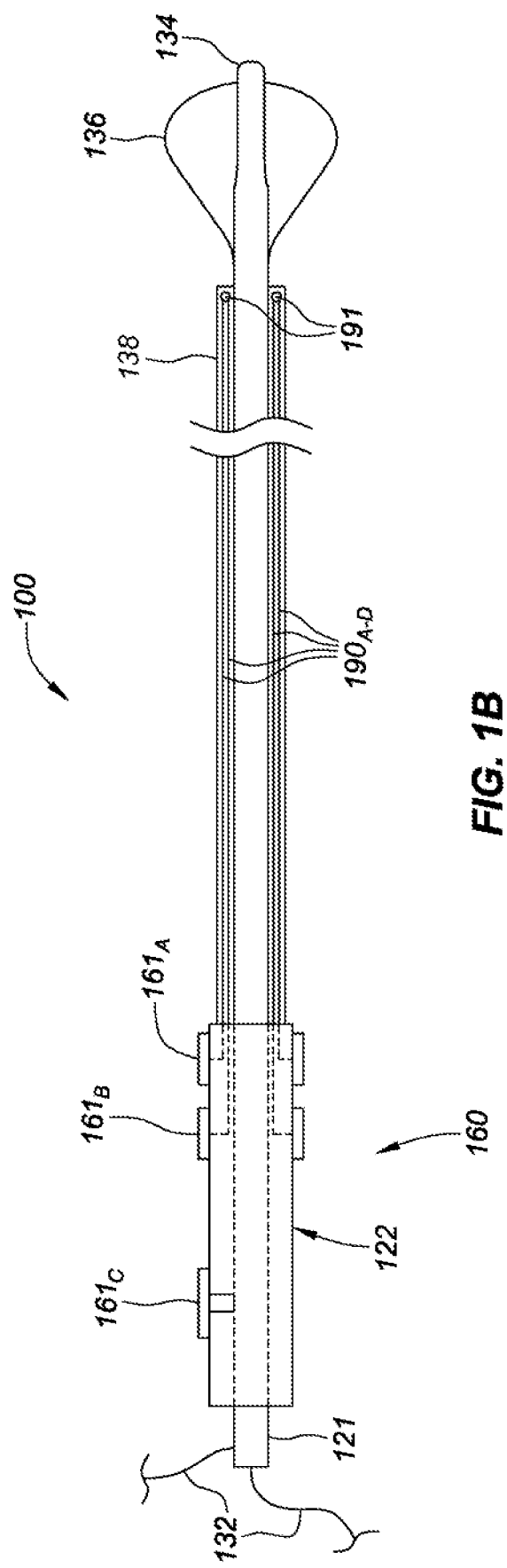
FIG. 1B is a cross-sectional side view of one implementation of the catheter system shown in FIG. 1A, consistent with various aspects of the present disclosure.

FIG. 1B is a cross-sectional side view of one implementation of an ablation catheter 160 of the catheter system 100 shown in FIG. 1A. In the present embodiment, a distal end of the ablation catheter 160 includes a balloon 136 that may be delivered and inflated near a target portion of a patient's body via the cardio-vasculature system. The balloon 136 may be stored during delivery within an interstitial space between inner shaft 134 and delivery sheath 138 (also referred to as a steerable catheter sheath). Pull wires $190_{A-D}$, extending a length of the outer sheath 138, and coupled to one or more pull rings 191 near a distal end of the ablation catheter 160 facilitate positioning of the distal portion of the catheter in proximity to the target. A handle 122 of ablation catheter 160 may include rotary actuators $161_{A-B}$ which facilitate manipulation of the pull wires $190_{A-D}$, and thereby steer a distal end of the sheath 138. To facilitate deployment of the ablation balloon 136, a clinician, upon arriving at the target location, may manipulate linear actuator 161$_C$ (also referred to as a slider) to extend a distal end of inner shaft 134 out of sheath 138 (as shown in FIG. 1B).

Once the ablation balloon 136, coupled to inner shaft 134, has extended out of the sheath 138, the balloon may be inflated and extended into contact with tissue targeted for ablation (e.g., an ostium of a pulmonary vein).

A proximal end of ablation catheter 160 may include a cable connector or interface 121 coupled to handle 122 which facilitates coupling the ablation catheter 160 to other elements of the catheter system 100 (e.g., irrigation subsystem 181, vacuum/leak detection subsystem 182, and electrical monitoring system 183, as shown in FIG. 1A) via cables 132.

Figure 2:
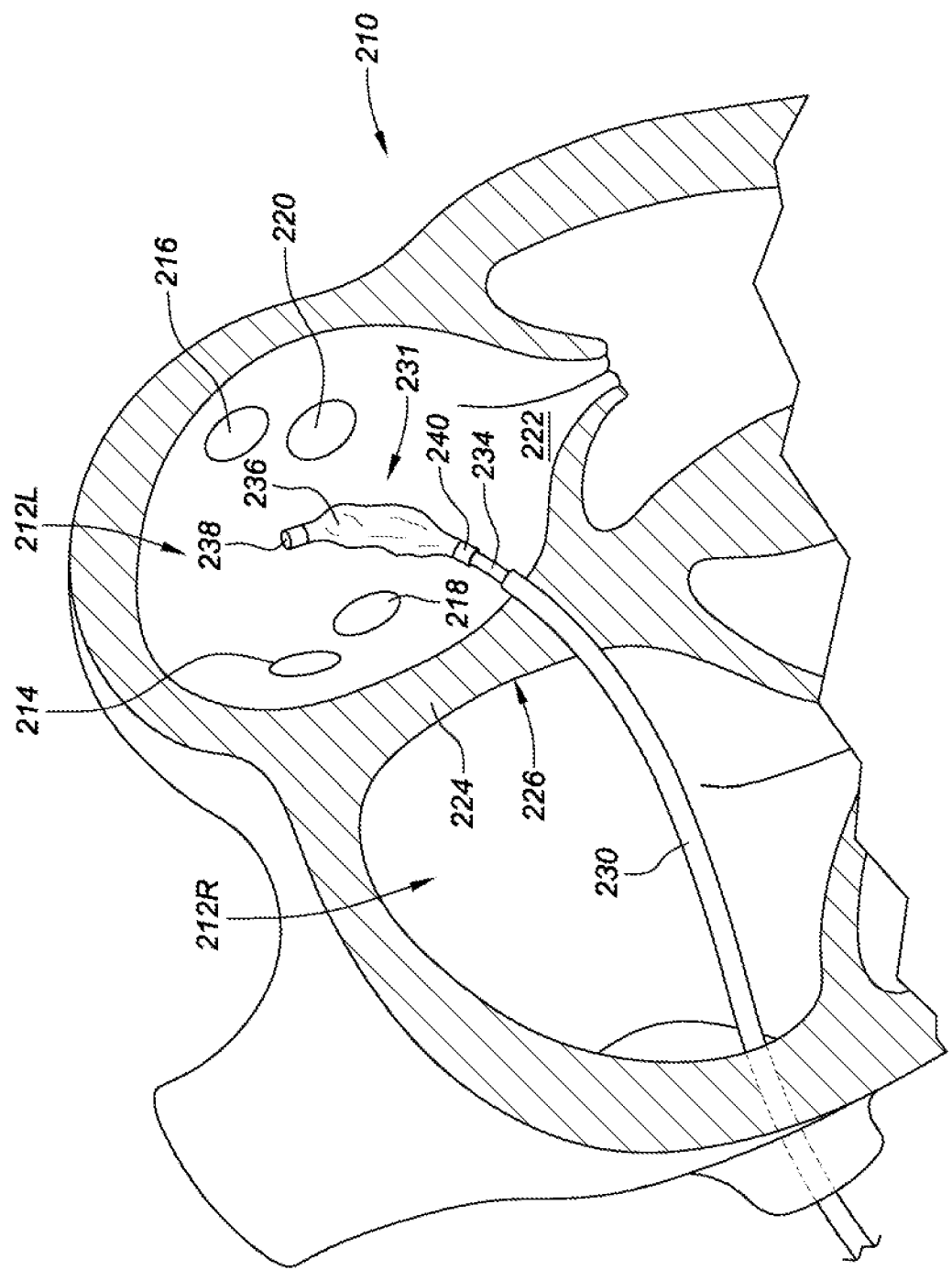
FIG. 2 is a partial cross-sectional front view of a cardiac muscle with a pulmonary vein isolation balloon catheter locating a pulmonary vein, consistent with various aspects of the present disclosure.

FIG. 2 is a cross-sectional front-view of a portion of cardiac muscle 210 with an ablation balloon catheter 231 locating a pulmonary vein (e.g., 214, 216, 218, and 220) for performing therapy for a cardiac arrhythmia, such as atrial fibrillation. As shown in FIG. 2, the cardiac muscle 210 includes two upper chambers called left atrium 212L and right atrium 212R, and two lower chambers called the left ventricle and right ventricle (partially shown).

Aspects of the present disclosure are directed to ablation therapies in which myocardial tissue in pulmonary veins 214, 216, 218, and 220, which form conductive pathways for electrical signals traveling through the tissue, is destroyed in order to electrically isolate sources of unwanted electrical impulses (arrhythmogenic foci) located in the pulmonary veins. By either destroying the arrhythmogenic foci, or electrically isolating them from the left atrium 212L, the symptoms of the arrhythmia can be reduced or eliminated.

In an exemplary embodiment of the present disclosure, an ablation balloon catheter 231 may be introduced into the left atrium 212L by a steerable catheter sheath 230 (commonly referred to as an introducer). An inner shaft 234 may guide the catheter tip 238 once introduced into the left atrium by the sheath 230. Optionally, the ablation balloon catheter may include mapping electrodes 240 at a distal end of the ablation balloon catheter 231. In operation, the sheath 230 has its distal end positioned within left atrium 212L. As shown in FIG. 2, a transseptal approach 226 may be utilized in which the introducer sheath is introduced through a peripheral vein (typically a femoral vein) and advanced to right atrium 212R. The transseptal puncture kit makes a small incision into the fossa ovalis 224 which allows the distal end of the sheath 230 to enter the left atrium 212L.

In other embodiments, ablation balloon catheter 231 may be introduced into left atrium 212L through the arterial system. In that case, introducer sheath is introduced into an artery (such as a femoral artery) and advanced retrograde through the artery to the aorta, the aortic arch, and into the left ventricle. The ablation balloon catheter 231 is then extended from within a lumen of the sheath 230 to enter the left atrium through mitral valve 222.

Once sheath 230 is in position within left atrium 212L, steerable ablation balloon catheter 231 is advanced out a distal end of the sheath and toward one of the pulmonary veins (e.g., 214, 216, 218, and 220). In FIG. 2, the target pulmonary vein is right superior pulmonary vein 214. Steerable sheath 230 of the ablation balloon catheter may be manipulated until the distal tip 238 of the ablation balloon catheter is substantially aligned with a longitudinal axis of the target pulmonary vein 214, after which the ablation balloon 236 is expanded and extended into contact with the target pulmonary vein 214.

Carried near a distal end 238 of ablation balloon catheter 231, ablation balloon 236 remains in a collapsed condition so that it may pass through sheath 230, and enter left atrium 212L. Once in the left atrium, the ablation balloon 236 is extended out of introducer sheath 230, deployed, and extended into contact with target pulmonary vein 214. The catheter shaft 234 may include steerable elements that allow for precisely positioning the balloon 236.

Optionally, ablation balloon catheter 231 may include mapping electrodes 240 at a distal end 238 of ablation balloon catheter 231. The mapping electrodes may be ring electrodes that allow the clinician to perform a pre-deployment electrical mapping of the conduction potentials of the pulmonary vein. Alternatively, mapping electrodes may be carried on-board a separate electrophysiology catheter, which may extend through a guidewire lumen that extends through a length of catheter shaft 234. In some specific embodiments, the distal end 238 may include electrodes that may be utilized for touch-up radio-frequency ablation, following a cryoablation treatment for example.

In one exemplary embodiment of the present disclosure, to ablate tissue surrounding the ostia of pulmonary vein 214, once the balloon 236 is deployed, a manifold within the balloon fills with a super-cooled liquid (e.g., a cryogenic fluid) that is distributed to cool the targeted tissue of the pulmonary vein 214 in response to a phase-change of the liquid to a gas within the balloon in response to a pressure drop within the balloon.

Figure 3:
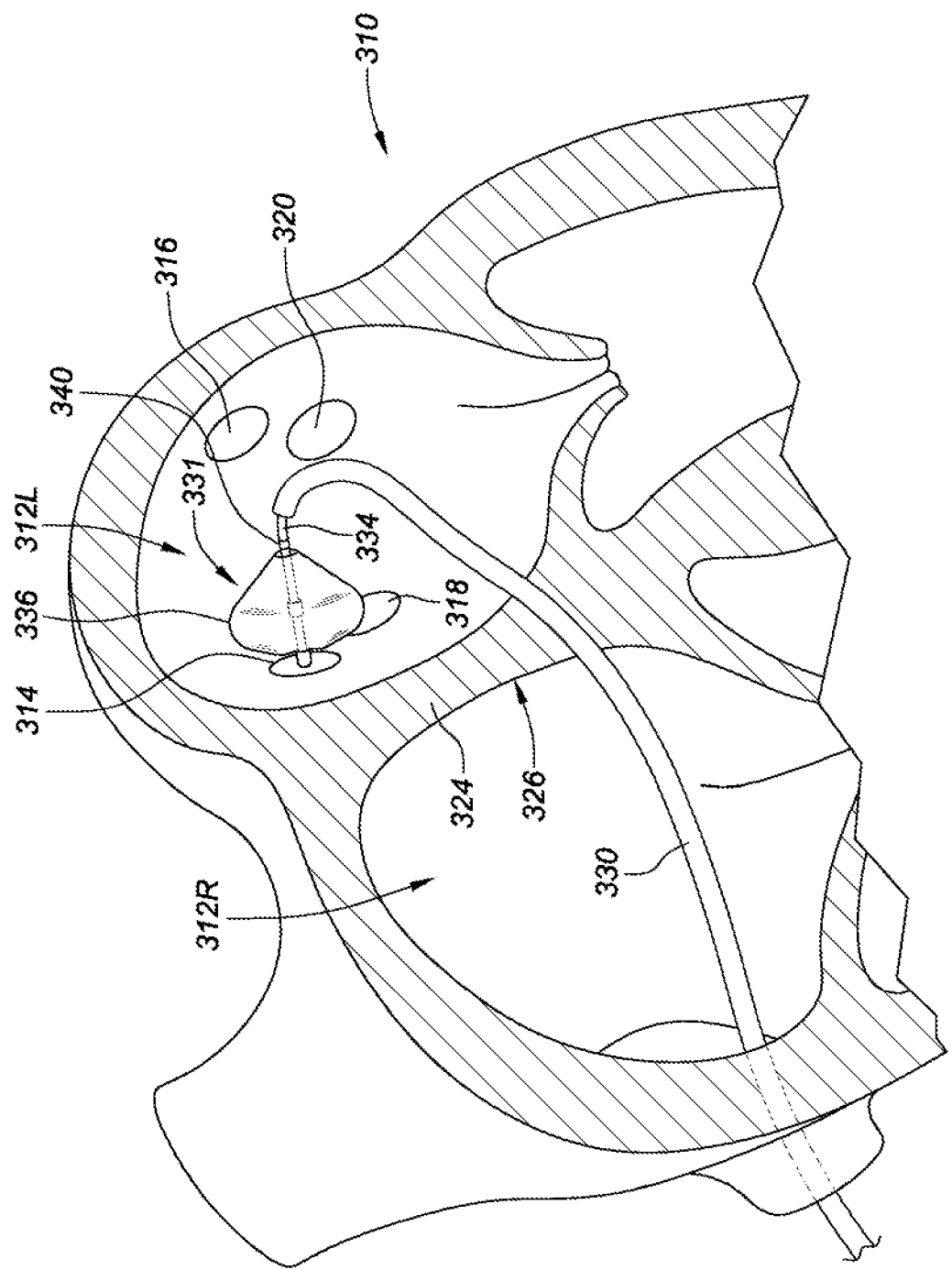
FIG. 3 is a partial cross-sectional front view of a cardiac muscle with a deployed pulmonary vein isolation balloon catheter extended into contact with an antral portion of a pulmonary vein, consistent with various aspects of the present disclosure.

FIG. 3 shows an ablation balloon catheter 331 including an ablation balloon 336 advanced through cardiac muscle 310 and into contact with an ostia of pulmonary vein 314 (or one of the other pulmonary veins 316, 318, and 320). In FIG. 3, a catheter sheath 330 has been extended through right atrium 312R and fossa ovalis 324 (and may be anchored to a wall 326 of the fossa ovalis). The catheter sheath 330, once inside left atrium 312L, to make contact with some of the pulmonary veins (e.g., 314 and 318) must be manipulated by a clinician to make a tight corner near a distal end of the catheter sheath 330. Once aligned with the target pulmonary vein 314, the balloon 336 and a distal portion of catheter shaft 334 may be extended out of the catheter sheath 330 and the balloon 336 expanded before making contact with the ostia of the target pulmonary vein 314. As the ablation balloon catheter contacts the pulmonary vein, mapping may be conducted using electrodes 340 (within or adjacent to the ablation balloon) in order to verify proper location prior to deployment of the ablation balloon, as well as confirm diagnosis prior to conducting an ablation therapy.

To expand the balloon 336 of ablation balloon catheter 331, a flow of cryogenic fluid is released into an interior of the balloon via a manifold. Where the balloon suffers from a manufacturing defect, damaged during delivery through catheter sheath 330, exposes to an over-pressure condition, or otherwise, the balloon may be subject to leaking and/or failure which could potentially release cryogenic fluid into a patient's bloodstream (leading to injury and/or death, in some extreme cases). Accordingly, aspects of the present disclosure are directed to sensing conditions that may lead to a leak and/or failure of the balloon, or identifying the condition shortly thereafter. For example, in some embodiments the balloon 336 may include an inner and outer balloon with an interstitial space therebetween. In such embodiments, the interstitial space may be placed under a vacuum and a pressure sensor (which may also sense a vacuum, and/or a vacuum sensor) may be used to determine when the inner balloon has failed. Moreover, in some embodiments the inner balloon may be non-compliant and the outer balloon may be compliant to facilitate capture of expanded cryogen associated with a failure of the inner balloon. In yet other embodiments, both balloons may be compliant or non-compliant. In embodiments where both balloons are compliant, the inner and outer balloons may have the same material properties (e.g., burst pressure) and/or comprise the same material (e.g., Nylon 11, also known as Polyamide 11 or PA11), or Polyethylene terephthalate (also referred to as PET).

Figure 4:
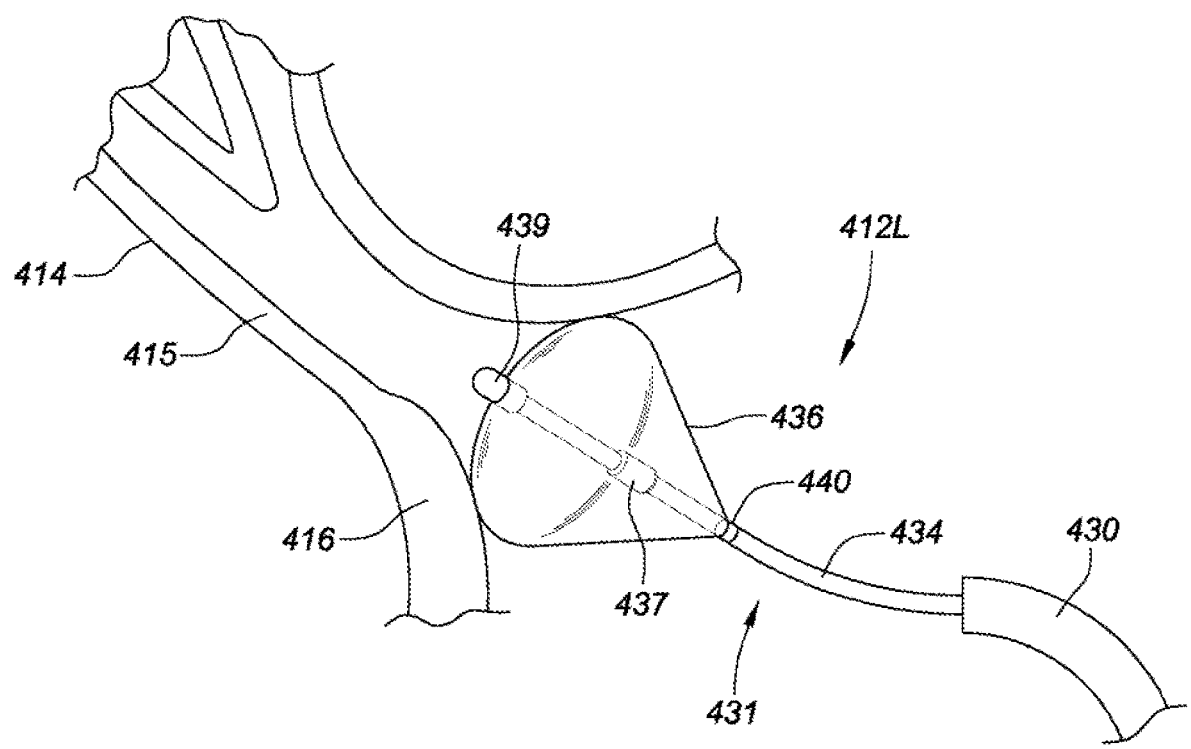
FIG. 4 is a cross-sectional view of a pulmonary vein with a deployed pulmonary vein isolation balloon catheter positioned in contact with the pulmonary vein antrum, consistent with various aspects of the present disclosure.

FIG. 4 shows ablation balloon catheter 431 with an ablation balloon 436 in contact with target pulmonary vein 414. Once steerable catheter sheath 430 has positioned the ablation balloon 436 into contact with the target pulmonary vein 414, the catheter shaft 434 may be extended away from catheter sheath 430. In the present embodiment, the balloon 436 is placed into contact with an ostia 416 of the target pulmonary vein (as opposed to an antrum 415). Electrophysiology electrodes 439 and 440 ("EP electrodes") may be used to determine the electrical flow through the pulmonary vein. To expand the balloon 436, cryogenic fluid is introduced to the balloon via manifold 437.

To diagnose a condition, monitor an ablation therapy, and confirm the efficacy of an ablation therapy, ablation balloon catheter 431 may include EP electrodes 439 and 440, at distal and proximal ends of ablation balloon 436, respectively. As a specific example, the EP electrodes may electrically map the pulmonary vein to determine whether it is associated with a source of electrical impulses that cause atrial arrhythmias with the cardiac muscle. Further, as many ablation treatments require multiple therapies in order to achieve a desired reduction of electrical impulse transmission between the target pulmonary vein and the left atrium 412L, the EP electrodes may confirm the efficacy of an ablation therapy by measuring the electrical signals adjacent the lesion line.

In some embodiments, electrodes 439 and 440 may be used to ensure occlusion of the pulmonary vein prior to initiating cryo-therapy delivery. When the balloon is properly occluding the pulmonary vein, the electrodes 439 and 440 will be conductively coupled to the myocardial tissue of the pulmonary vein and thereby transmit a signal to controller circuitry indicative of the contact.

As will be discussed in more detail in reference to FIG. 5A, deployment of ablation balloon 436 is achieved by pumping a fluid (gas or liquid) through inner shaft 434 (from a proximal to a distal end), and into the ablation balloon via manifold 437. Similarly, in embodiments utilizing cryogenic ablation methodologies, super-cooled fluid for ablating pulmonary venous tissue is pumped into the ablation balloon and ablates the tissue in contact with the ablation balloon (and in some cases in proximity therewith) by drawing heat from the tissue.

Due to the phase-change of the cryogenic-fluid that occurs within balloon 436, the volume of gas that must be exhausted from the balloon is many times the volume of fluid that is delivered to the balloon. In some embodiments, an exhaust lumen may be an annulus within catheter shaft 434 that facilitates a large cross-sectional area (e.g., the exhaust lumen may have a clover-leaf like shape). To further facilitate manufacturability and assembly of catheter shaft 434, additional lumens (e.g., vacuum lumen, cryo-delivery lumen, and a pressure-sensor lumen, for example) may be routed through the exhaust annulus. Such routing further facilitates a guidewire lumen to extend through an entire length of balloon catheter 431.

The ablation balloons 336/436, as shown in FIGS. 3 and 4, are depicted as being translucent (which allows for the visibility of internal components). However, it is to be understood that the ablation balloons 336/436, disclosed herein, may also be semi-translucent or opaque.

Figure 5:
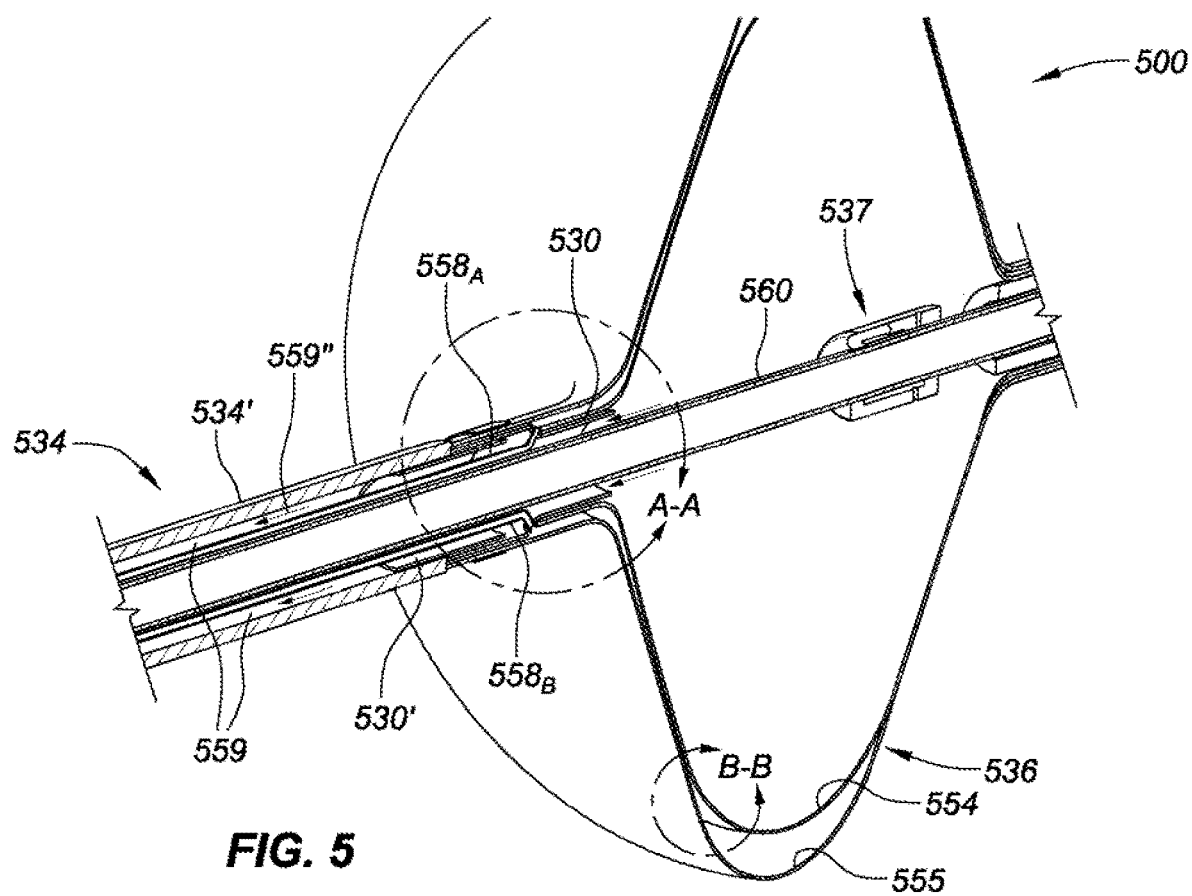
FIG. 5 is an isometric, cross-sectional side view of a distal portion of a pulmonary vein isolation balloon catheter, consistent with various aspects of the present disclosure.
Figure 5A:
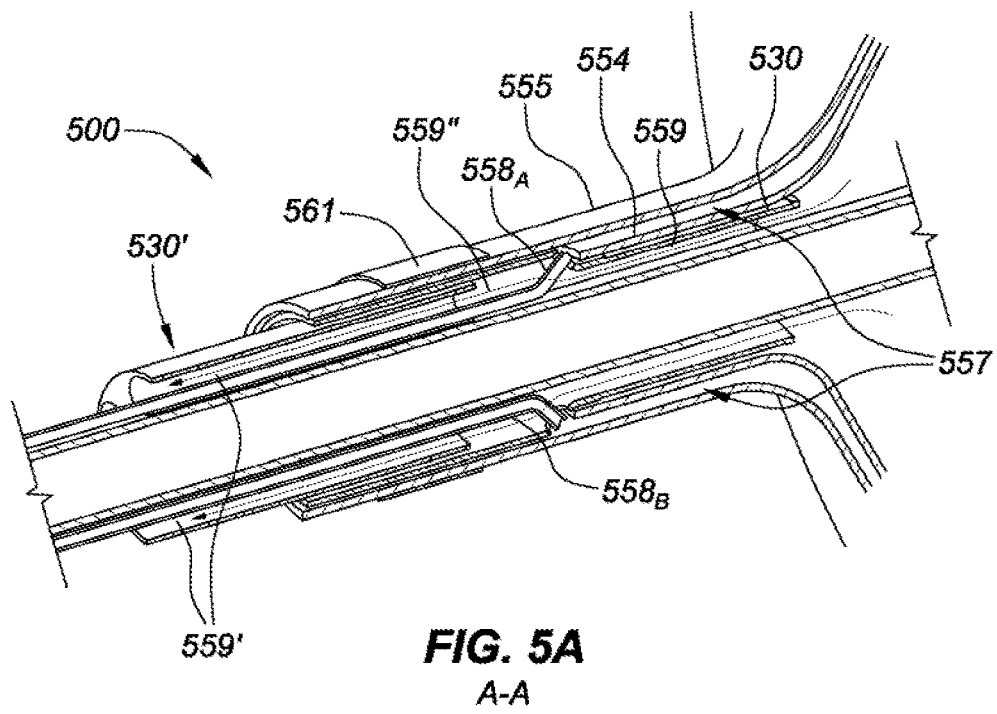
FIG. 5A is an isometric, cross-sectional side view of an adaptor of the pulmonary vein isolation balloon catheter of FIG. 5, consistent with various aspects of the present disclosure.

FIG. 5 is an isometric, cross-sectional side view of a distal portion of a pulmonary vein isolation balloon catheter 500 and FIG. 5A is an isometric, cross-sectional side view of an area in proximity to an adaptor 530 of the pulmonary vein isolation balloon catheter 500 of FIG. 5, consistent with various aspects of the present disclosure. A balloon 536 includes a first (inner) layer 554 within a second (outer) layer 555, which are coupled to an adaptor 530 at two radially and longitudinally offset locations to create an interstitial space between the first and second layers. The adaptor 530 may be circumferentially positioned between an outer and an inner catheter shaft (534' and 530, respectively). In various embodiments of the present disclosure the dual-layer balloon including first and second layers are two entirely separate balloons (e.g., inner and outer balloons).

The radially offset circumferential coupling locations of the first and second balloon layers 554 and 555, respectively, on adaptor 530 creates an interstitial space 557 therebetween. The interstitial space 557 extends circumferentially along (at least a portion of) a length of the balloon 536. The adaptor 530 also forms an exhaust lumen annulus 559 between inner and outer catheter shafts. During an ablation therapy, a cryo-liquid lumen may extend up through the exhaust lumen annulus 559 (similar to vacuum lumen 558A and pressure sensor lumen 558B) and be coupled with manifold 537 in such a way as to fluidly communicate the cryo-liquid thereto. Once the cryo-liquid is released from apertures in the manifold 537 that are distributed longitudinally and circumferentially about the manifold, the reduced pressure within first layer 554 of the balloon causes a phase-change of the cryo-liquid to a gas which absorbs a large amount of energy and cools the exterior surface of second layer 555. The cryogenic exhaust gases within the first layer 554 may then be exhausted through exhaust lumen annulus 559. The exhaust lumen 559 extends through adaptor 530, adaptor extension 530' which couples the balloon 536 and adaptor 530 to catheter shaft 534. The flow of exhaust through the distal portion of the balloon catheter 500 is shown via arrows 559". An annulus between the catheter shaft 534 and guidewire lumen 560 may run the remaining length of the catheter to the handle.

One or more ring electrodes 561 may be used to couple a first layer 554 of balloon 536 to adaptor 530, adaptor extension 530', among other components.

To prevent a failure mode of balloon 536 associated with a leak and/or rupture of a first layer 554, aspects of the present disclosure are directed to detecting a leak and/or rupture of the first layer 554 and mitigating risk to the patient by terminating the ablation therapy. In one example embodiment, an interstitial space 557 formed by adaptor 530 between first and second layers of the balloon 536, 554 and 555, respectively, is fluidly coupled to a vacuum lumen 558A and a pressure sensor lumen 558B. The vacuum lumen 558A induces a vacuum pressure within the interstitial space 557 during an ablation therapy. The pressure sensor lumen 558B is fluidly coupled with a pressure sensor which monitors a change in vacuum throughout the ablation therapy. Where the first layer 554 is not containing a cryogenic fluid within the balloon 536, the cryogenic fluid within the first layer of the balloon will be drawn into the interstitial space 557 thereby reducing a vacuum pressure therein which will be sensed by a pressure sensor. Controller circuitry of the ablation balloon catheter 500 may receive a signal from the pressure sensor indicative of the vacuum pressure within the interstitial space 557 at a given time. Where the controller circuitry identified a drop in vacuum pressure during the ablation therapy, the controller circuitry may take corrective measures to mitigate risk to the patient associated with such a leak. Importantly, where the first layer 554 of the balloon has ruptured, pressure within the interstitial space may rise eventually causing the second layer 555 to also fail—which would cause the dispersion of cryogenic fluid within the patient's bloodstream. Upon detecting a leak in first layer 554, the controller circuitry may take one or more of the following actions: disable further flow of cryogenic liquid into the balloon 536; release the pressure in the exhaust lumen; purge the cryogenic fluid in the cryogenic fluid lumen; and apply a vacuum pressure onto the exhaust lumen.

Figure 5B:
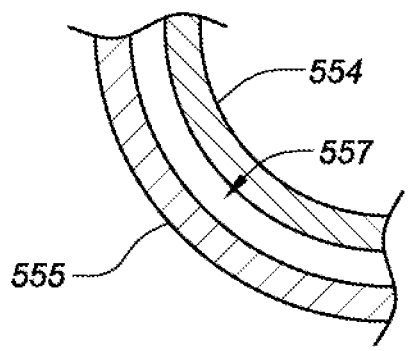
FIG. 5B is an isometric, side view of an interstitial space between inner and outer balloons of the pulmonary vein isolation balloon catheter of FIG. 5, consistent with various aspects of the present disclosure.

FIG. 5B is an isometric, side view of an interstitial space between first and second layers, 554 and 555, respectively, of balloon 536 of the pulmonary vein isolation balloon catheter 500 of FIG. 5, consistent with various aspects of the present disclosure. In some embodiments, the first layer 554 may comprise a material or composition of materials that facilitate a substantially non-conforming shape once expanded by the introduction of cryogenic fluid therein (e.g., nylon, polyethylene, polyurethane, etc.). The second layer 555 may comprise a material or composition of materials that facilitate a substantially conforming shape which facilitates the substantial expansion of the balloon 536 in response to a rupture of the first layer 554. The second layer may be either compliant or non-compliant. In some embodiments, the outer balloon may facilitate a larger volume, may be a compliant balloon that has the capacity to grow substantially in response to an inner balloon rupture, and/or be a non-compliant material with a higher rated burst pressure then the inner balloon. The interstitial space 557, during an ablation therapy, may be drawn into a vacuum pressure. While experiencing such a vacuum pressure the interstitial space 557 between the first and second layers may be infinitesimally small. However, a rupture or leak through the first layer 554 of the balloon and into the interstitial space 557 quickly changes the vacuum pressure therein. This change in pressure within the interstitial space 557 may be measured and used to identify such a balloon failure.

Figure 5C:
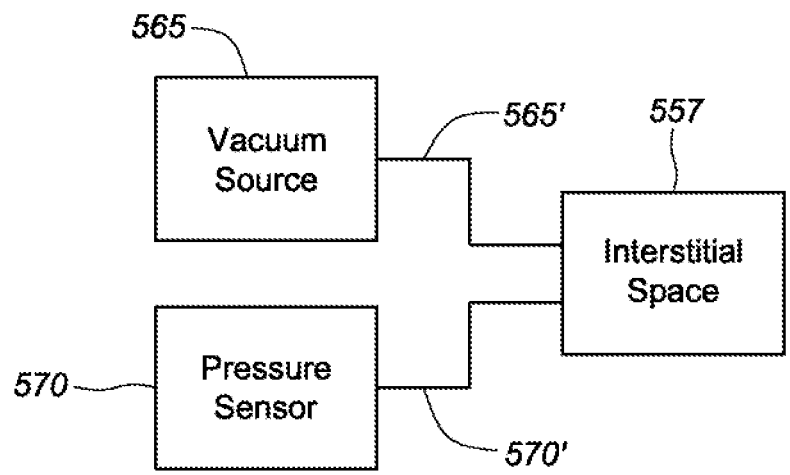
FIG. 5C is a diagrammatic view of a safety system for the pulmonary vein isolation balloon catheter of FIG. 5, consistent with various aspects of the present disclosure.

FIG. 5C is a diagrammatic view of a safety system for the pulmonary vein isolation balloon catheter 500 of FIG. 5, consistent with various aspects of the present disclosure. A vacuum source 565 is fluidly coupled, via a first fluid path 565', to an interstitial space 557 between first and second layers of a dual-layer balloon.

Figure 5D:
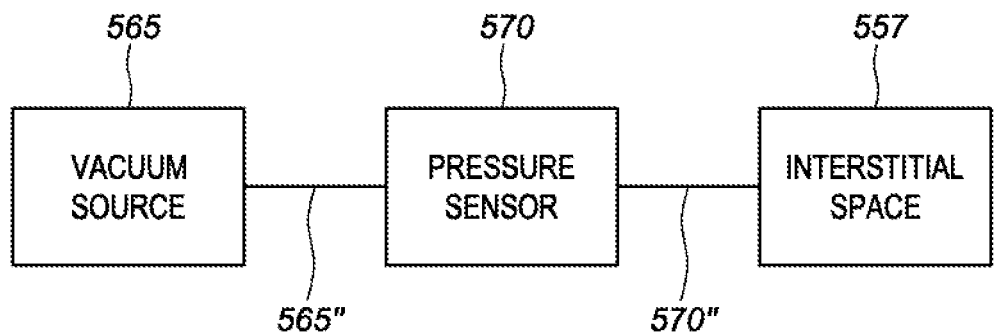
FIG. 5D is a diagrammatic view of an alternative safety system for the pulmonary vein isolation balloon catheter of FIG. 5, consistent with various aspects of the present disclosure.

In some embodiments as disclosed in reference to FIG. 5D, it may be convenient, structurally, to measure a vacuum pressure in-line with a lumen extending between interstitial space 557 and vacuum source 565. In such an embodiment, the pressure sensor 570 may be fluidly coupled between a first fluid path 570" extending from the interstitial space and a second fluid path 565" extending to the vacuum source. Where the first and second fluid paths have the same inner diameter, a leak may be detected by the pressure sensor in as little as 1 second. In more preferred embodiments, a first fluid path 570" may have a larger diameter than a second fluid path 565"—facilitating increased leak response time. For example, where the first fluid path has an inner diameter of 0.016" and the second fluid path has an inner diameter of 0.008", a change in vacuum pressure within the interstitial space 557 may be detected by the pressure sensor 570 in as little as 50 milliseconds. In yet other embodiments, the pressure sensor 570 may be located within the interstitial space itself, a catheter handle, or within the capital equipment.

In embodiments consistent with FIG. 5C, to decrease detection time of a change in vacuum pressure within the interstitial space 557, which is indicative of a leak within one or more layers of the balloon, a second fluid path 570' may extend between the interstitial space 557 and a pressure sensor 570. Experimental results have demonstrated that the embodiment of FIG. 5C may reduce detection time of a leak into the interstitial space 557 by almost 50%. That is, the FIG. 5C configuration may detect leaks in less than 25 milliseconds.

Figure 6:
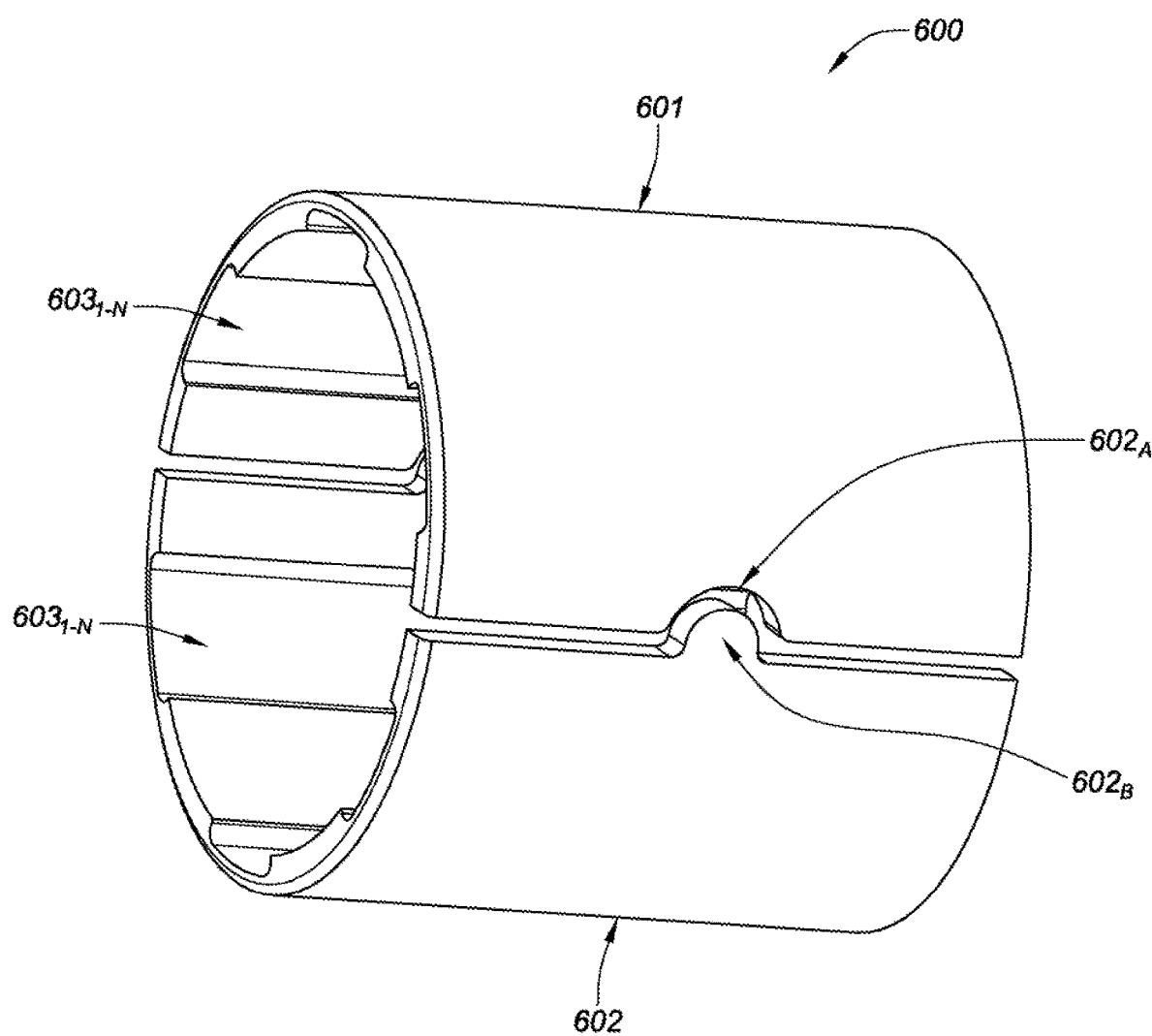
FIG. 6 is an isometric view of a spacer assembly, consistent with various aspects of the present disclosure.

FIG. 6 is an isometric view of a spacer assembly 600, consistent with various aspects of the present disclosure. The spacer assembly 600 includes a upper spacer 601 and a lower spacer 602 which may be coupled to one another via coupling features $602_{A-B}$. The spacer assembly 600 may be circumferentially coupled around an outer diameter of a first balloon layer to hold the balloon in place. Further, the spacer assembly may facilitate radially off-setting the first and second balloon layers near a proximal end of a balloon assembly, which may otherwise be drawn together by a vacuum pressure applied to an interstitial space between the first and second layers of the balloon. The upper spacer 601 and the lower spacer 602 may be crimped to one another, laser welded, ultrasonically welded spot welded, adhered, fastened via fasteners, or otherwise coupled to one another using techniques known in the art. The spacer assembly 600 includes channels $603_{1-N}$ circumferentially distributed along an inner diameter, where each channel extends longitudinally along a central axis thereof. The channels $603_{1-N}$ maintain a space between the first and second layers of the balloon for drawing a vacuum within the interstitial space. In some embodiments, absent the spacer assembly 600, a vacuum may be drawn in a proximal interstitial space between the first and second layers, sealing the first and second layers of the balloon to one another, without creating a vacuum at an intermediate and/or distal region of the interstitial space. The spacer assembly 600 of FIG. 6, facilitates drawing a complete vacuum within the interstitial space (as discussed in more detail in reference to FIGS. 7-7A).

Figure 7:
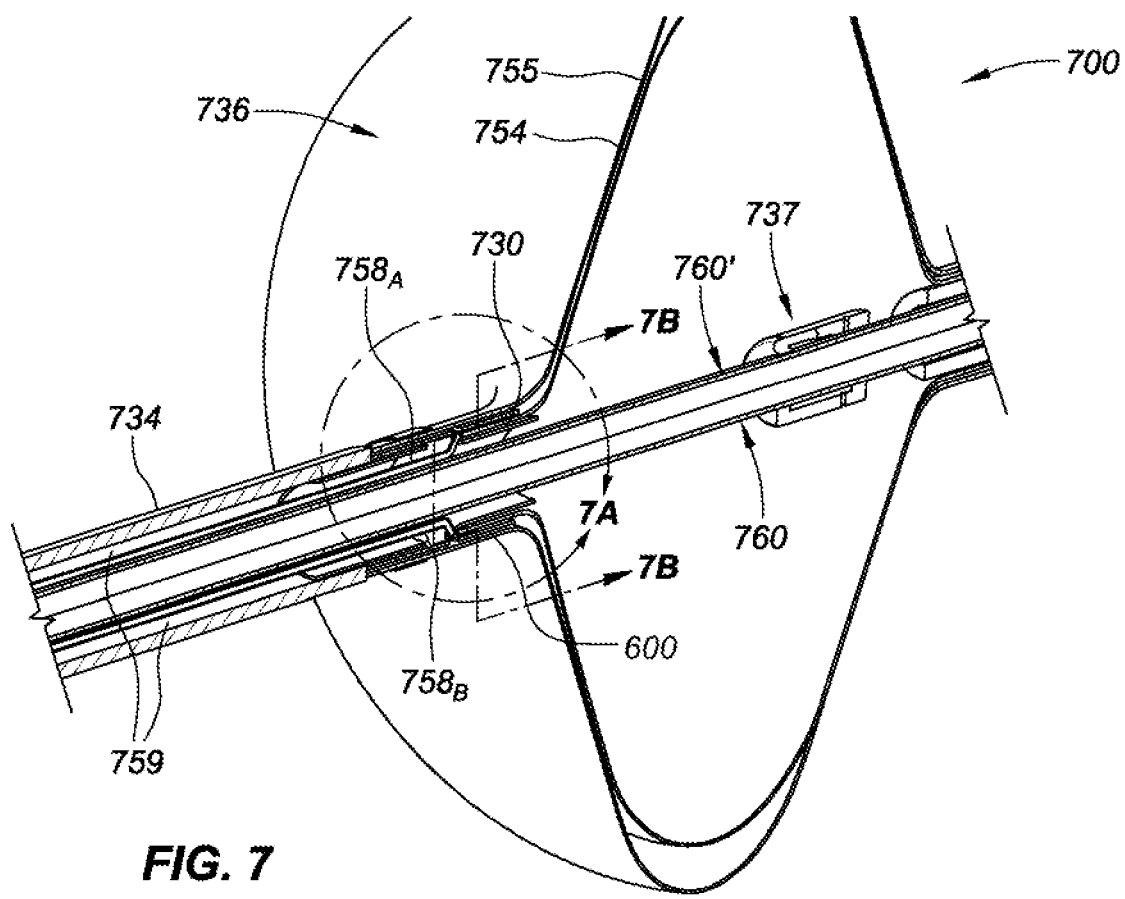
FIG. 7 is an isometric, cross-sectional side view of a distal portion of a pulmonary vein isolation balloon catheter, consistent with various aspects of the present disclosure.
Figure 7A:
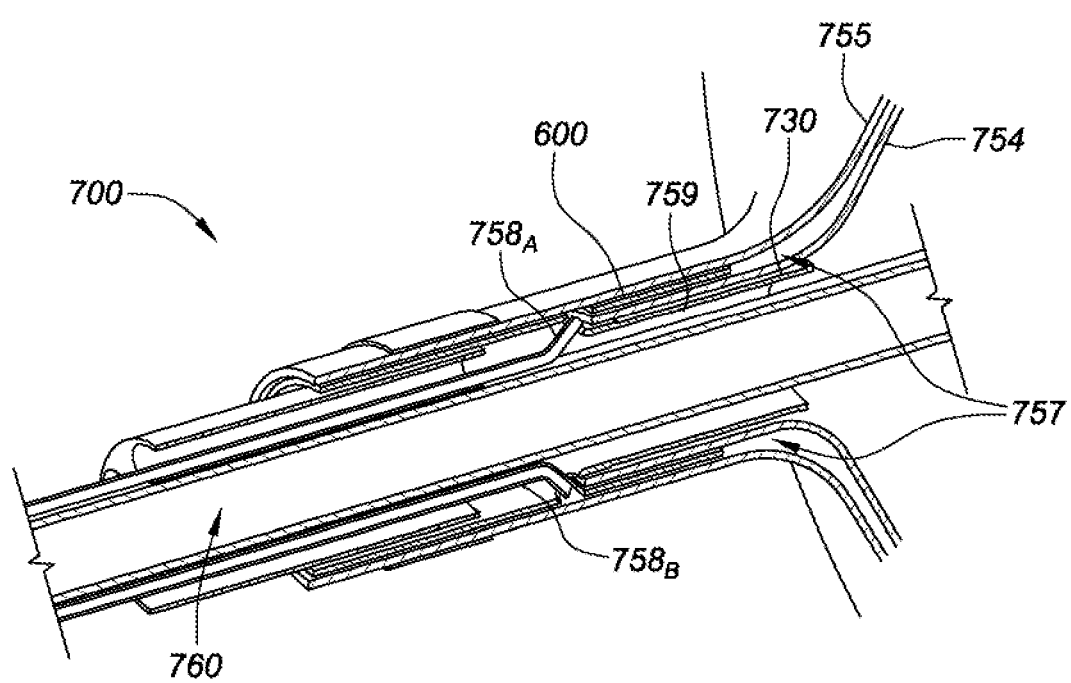
FIG. 7A is an isometric, cross-sectional side view of the pulmonary vein isolation balloon catheter of FIG. 7 including a spacer assembly, consistent with various aspects of the present disclosure.

FIG. 7 is an isometric, cross-sectional side view of a distal portion of a pulmonary vein isolation balloon catheter 700, and FIG. 7A is an isometric, cross-sectional side view of the pulmonary vein isolation balloon catheter of FIG. 7 including a spacer assembly.

In one exemplary embodiment of the isolation balloon catheter 700, after being introduced into a left atrium of a cardiac muscle, the balloon 736 may be deployed by injecting a cryogenic fluid through fluid lumen 760', which extends through a length of the catheter shaft 734 and into a fluid manifold 737 and out one or more apertures in the manifold and into a cavity of a first layer 754 of the balloon 736. The fluid lumen 760' may be coupled to an exterior of guidewire lumen 760. The fluid manifold 737 may be positioned at a distal end of the balloon 736. Once deployed, the ablation balloon 736 may be moved into contact with myocardial tissue and cooled/heated fluid may be injected into the cavity through one or more ports. In very specific embodiments, the ports may include nozzles or other fluid-flow controlling features that direct the flow, and control the velocity, of the fluid exiting the port toward specific target areas on the balloon 736; for example, where the myocardial tissue to be ablated is likely to contact the ablation balloon. In the present embodiment, the balloon 736 is substantially bell-shaped (or conically shaped) to provide additional antral contact with target myocardial tissue of a pulmonary vein, and may facilitate more patient-to-patient anatomical and position variation of the pulmonary veins.

To control the pressure exerted on the ablation balloon by cryogenic fluid injected into the balloon via the fluid manifold 737, an exhaust lumen annulus 759 along a length of inner shaft 734 may exhaust fluid from within the balloon 736. For example, the exhaust lumen annulus 759 may receive fluid from within the ablation balloon and deliver the fluid through a length of the shaft 734 to a handle with a reservoir or other means of discarding the fluid. In exemplary embodiments of the present disclosure utilizing cryogenic fluid to ablate the myocardial tissue in contact with the ablation balloon, a closed-loop system may be utilized to scavenge the cryogenic fluid, re-pressurize, and return to a tank for later use. In such a closed-loop system, cryogenic fluid may be pumped from a handle of a catheter system through a lumen in the inner shaft to the fluid manifold and circulated around the ablation balloon. Once circulated through the ablation balloon, the exhaust lumen annulus 759 draws the fluid back to the handle portion of the catheter system where the fluid is re-pressurized before being injected back into the ablation balloon to continue ablating tissue in contact with the ablation balloon.

Once an ablation therapy is complete, exhaust lumen annulus 759 may be coupled to a vacuum to draw out any remaining fluid within ablation balloon 736, thereby collapsing the ablation balloon. The ablation balloon 736 and shaft 734 may then be retracted into a steerable sheath.

Various embodiments of the present disclosure may further include leak prevention and detection measures to prevent against fluid leaking out of ablation balloon 736 into a patient's blood pool. This is particularly advantageous where the cryogenic fluid is a gas (e.g. nitrous-oxide) that may cause negative health affects when introduced into a patient's bloodstream, including pulmonary embolisms and stroke. In the exemplary embodiment depicted in FIGS. 7-7A, first and second layers 754 and 755, respectively, provide additional protection against fluid leakage into the patient's blood pool. Specifically, if the first or second layer is perforated or otherwise rendered incapable of containing a fluid within the ablation balloon 736, the other layer may act as a barrier to fluid escape. As an added measure, a leak detection circuit (see, e.g., 5C and discussion thereof) may be utilized to detect fluid in an interstitial space 757 between the first and second layers. Accordingly, if the first layer is perforated, the fluid flows into the interstitial space 757, and is drawn toward vacuum lumen $758_A$, via channels 603 (shown in FIG. 6) within spacer assembly 600. The egress of liquid into the interstitial space 757 is detected by a pressure sensor which may communicate the change of vacuum pressure with controller circuitry of the isolation balloon catheter 700. The controller circuitry may then take one or more corrective actions.

Figure 7B:
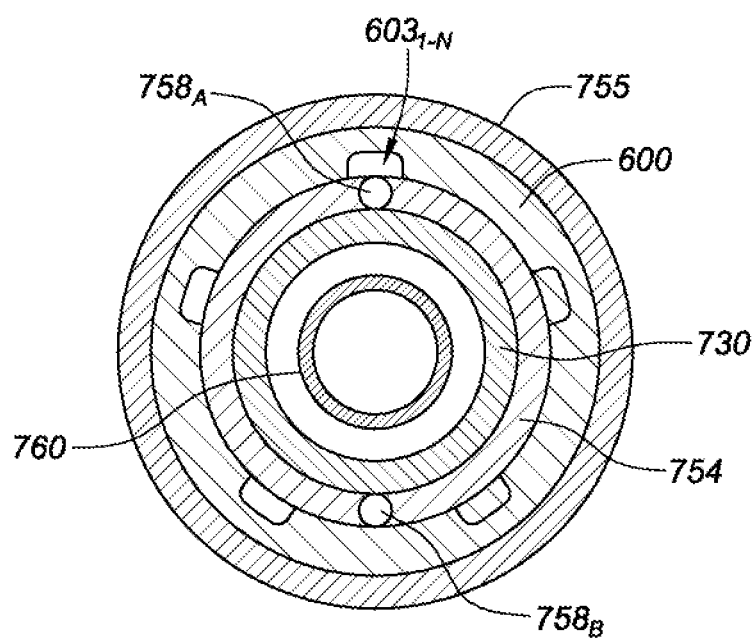
FIG. 7B is a cross-sectional front view of the pulmonary vein isolation balloon catheter of FIG. 7, consistent with various aspects of the present disclosure.

As shown in FIG. 7B, a cross-sectional front view of the pulmonary vein isolation balloon catheter of FIG. 7, the spacer assembly 600 facilitates continuous fluid communication between vacuum lumen $758_A$, pressure sensor lumen $758_B$, and interstitial space 757. Though adaptor 730 radially and longitudinally offsets the mounting points of the first and second layers 754 and 755, respectively, of balloon 736 the layers may still be drawn together and create a seal between the lumens $758_{A-B}$ and interstitial space 757. Spacer assembly 600 (and inner diameter channels 603 thereof) maintains the radial offset of the first and second layers of the balloon to prevent such a seal between the first and second layers. Without spacer assembly 600, a vacuum pressure may be sensed by a pressure sensor, but not be (adequately) applied to the interstitial space—greatly increasing response time and/or negating a response all together of a leak detection circuit to liquid ingress into the interstitial space 757.

Channels 603 of spacer assembly 600 force a vacuum to extend entirely through an interstitial space 757 within the balloon, as opposed to merely extending a vacuum through the most direct route between vacuum lumen $758_A$ and pressure sensor lumen $758_B$. The most direct route, between the two lumens, is sealed off by spacer assembly 600.

Ablation balloons have been developed for a variety of different applications and take a number of different forms. Aspects of the present disclosure may utilize ablation balloons of various types and different mechanical construction. The ablation balloons may be either of an electrically or thermally conductive material, and can be either self-erecting or mechanically erected, such as through the use of an internal balloon.

Pulmonary vein isolation balloon catheters as disclosed herein may include a handle at a proximal end of a catheter shaft, with the catheter shaft being introduced into a patient's cardiovascular system via an introducer sheath (such as St. Jude Medical, Inc.'s Agilis™ NxT Steerable Introducer sheath).

Various catheter shaft designs consistent with the present disclosure may include a multi-lumen design which allows for input and output flows of cryogenic fluid, electrical lead wires, and guide wires for steering the distal end of the shaft. In some embodiments, three lumens may be radially offset within the shaft from a guidewire lumen. In yet other embodiments, all of the lumens may be radially and circumferentially distributed about a longitudinal axis of the shaft.

In various embodiments of the present disclosure, an ablation balloon is capable of conducting ablation therapy at more than one location of the ablation balloon. For example, energy can be delivered to a proximal, distal, or intermediary portion of the ablation balloon. In some embodiments, the proximal, distal, intermediary portions, or combinations thereof may simultaneously conduct ablation therapy. In more specific embodiments, the amount of ablation therapy (e.g., energy transmitted to the tissue) conducted at a tissue location may be controlled individually.

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Additional information and examples can be found in U.S. Provisional Application No. 62/432,065, filed on Dec.

9, 2016, U.S. Provisional Application No. 62/578,201, filed on Oct. 27, 2017, U.S. Provisional Application No. 62/578,320, filed on Oct. 27, 2017, U.S. Provisional Application No. 62/578,325, filed on Oct. 27, 2017, and U.S. Provisional Application No. 62/578,178, filed on Oct. 27, 2017, each of which is hereby incorporated by reference as if set forth fully herein.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation catheter system comprising:
    a catheter shaft including proximal and distal ends;
    a dual cryogenic ablation balloon coupled to the distal end of the catheter shaft, the dual cryogenic ablation balloon including an inner and an outer balloon;
    an interstitial space between the inner and outer balloons configured and arranged to capture cryogenic fluid that escapes from an internal cavity of the inner balloon;
    a manifold configured and arranged to deliver cryogenic fluid to the internal cavity of the inner balloon;
    a first and second lumen in fluid communication with the interstitial space; and
    an adaptor that mechanically couples the inner and outer balloons to the catheter shaft, and radially and longitudinally offsets proximal portions of the inner and outer balloons, wherein the adaptor is circumferentially positioned within the catheter shaft; and
    a spacer coupled between proximal portions of the inner and outer balloons, at least a portion of the spacer surrounding the adapter.

2. The ablation catheter system of claim 1, wherein the first lumen is a vacuum lumen configured and arranged to draw a vacuum within the interstitial space and to draw captured cryogenic fluid out of the interstitial space and into the vacuum lumen.

3. The ablation catheter system of claim 2, wherein the spacer is configured and arranged to maintain the interstitial space between the inner and outer balloons in response to a vacuum pressure within the interstitial space; and
    wherein the spacer includes a plurality of channels that extend into an inner diameter of the spacer and along a length of the spacer, the plurality of channels are configured and arranged to facilitate the flow of a fluid between the interstitial space and the vacuum lumen.

4. The ablation catheter system of claim 3, wherein the spacer includes a first and second portion, the first and second portions configured and arranged to be assembled about a circumference of the proximal portion of the inner balloon and coupled thereto.

5. The ablation catheter system of claim 1, wherein the second lumen is a pressure sensor lumen in fluid communication with a pressure sensor configured and arranged to sense a change in vacuum pressure within the interstitial space associated with a flow of cryogenic fluid through the inner balloon via the pressure sensor lumen.

6. The ablation catheter system of claim 1, wherein the interstitial space extends between the radially offset inner and outer balloons, the interstitial space is configured and arranged to capture cryogenic fluid that escapes the inner balloon;
the first lumen extends a length of the catheter shaft and through the adaptor into fluid communication with the interstitial space at a first end of the first lumen and a vacuum source at a second end of the first lumen, the first lumen configured and arranged to draw a vacuum within the interstitial space and to draw the captured cryogenic fluid out of the interstitial space,
the second lumen is in fluid communication with a pressure sensor, the second lumen configured and arranged to sense a change in vacuum pressure within the interstitial space associated with a flow of cryogenic fluid through the inner balloon and into the interstitial space; and
the catheter system further includes
a cryogenic fluid tank,
a cryogenic fluid lumen in fluid communication with the cryogenic fluid tank at a first end of the cryogenic fluid lumen, the cryogenic fluid lumen extends through a length of the catheter shaft and into fluid communication with the manifold at a second end of the cryogenic fluid lumen, and
controller circuitry communicatively coupled to the pressure sensor, and configured and arranged to control the flow of cryogenic fluid to the manifold in response to the change in vacuum pressure measured by the pressure sensor.

7. The ablation catheter system of claim 1, further including an exhaust lumen in fluid communication with the internal cavity of the balloon, the exhaust lumen extending a length of the catheter shaft and configured and arranged to exhaust cryogenic fluid out of the internal cavity.

8. The ablation catheter system of claim 7, wherein at least a portion of the length of the exhaust lumen has a clover-leaf-like cross-sectional area.

9. The ablation catheter system of claim 7, further including a guidewire lumen that extends through a length of the catheter shaft and ablation balloon; and wherein at least a portion of the length of the exhaust lumen forms an annulus between the outer diameter of the guidewire lumen and the outer diameter of the catheter shaft.

10. The ablation catheter system of claim 9, wherein the exhaust lumen has a clover-leaf-like cross-sectional area.

11. The ablation catheter system of claim 1, wherein the first lumen is configured and arranged to draw a vacuum within the interstitial space and to draw captured cryogenic fluid out of the interstitial space;
the second lumen is configured and arranged to sense a change in vacuum pressure within the interstitial space associated with a flow of cryogenic fluid through the inner balloon; and a spacer coupled between proximal portions of the inner and outer balloons, the spacer configured and arranged to maintain the interstitial space between the inner and outer balloons in response to a vacuum pressure within the interstitial space, the spacer includes a plurality of channels that extend into an inner diameter of the channel and along a length of the spacer, the plurality of channels are configured and arranged to facilitate the flow of a fluid between the interstitial space, the first lumen, and the second lumen.

12. A dual-layer ablation balloon comprising:
an inner balloon including an internal cavity configured and arranged to receive a cryogenic fluid in a liquid state and to facilitate a state transfer of the cryogenic into a gaseous state;
an outer balloon that encapsulates the inner balloon;
an interstitial space between the inner and outer balloons; and
an exhaust lumen in fluid communication with the internal cavity of the inner balloon, the exhaust lumen configured to exhaust the gaseous state cryogenic fluid out of the internal cavity, wherein at least a portion of the length of the exhaust lumen has a clover-leaf-like cross-sectional area; and
a spacer coupled between proximal portions of the inner and outer balloons, at least a portion of the spacer surrounding an adapter that mechanically couples the inner and outer balloons to a catheter shaft.

13. The dual-layer ablation balloon of claim 12, wherein the spacer is configured to maintain the interstitial space between the inner and outer balloons in response to a vacuum pressure within the interstitial space;
wherein the interstitial space is configured and arranged to capture cryogenic fluid that escapes from the internal cavity of the inner balloon.

14. The dual-layer ablation balloon of claim 13, further including a vacuum lumen in fluid communication with the interstitial space, the vacuum lumen configured and arranged to draw a vacuum within the interstitial space and to draw the captured cryogenic fluid out of the interstitial space and into the vacuum lumen.

15. The dual-layer ablation balloon of claim 14, further including a pressure sensor lumen in fluid communication with the interstitial space, the pressure sensor configured and arranged to sense a change in vacuum pressure within the interstitial space via the pressure sensor lumen, the change in vacuum pressure associated with a flow of cryogenic fluid through the inner balloon.

16. A dual-layer ablation balloon comprising:
an inner balloon including an internal cavity configured and arranged to receive a cryogenic fluid in a liquid state and to facilitate a state transfer of the cryogenic into a gaseous state;
an outer balloon that encapsulates the inner balloon;
an interstitial space between the inner and outer balloons;
an adaptor that mechanically couples the inner and outer balloons to a catheter shaft, and radially and longitudinally offsets proximal portions of the inner and outer balloons, wherein the adaptor is configured to be circumferentially positioned within a catheter shaft; and
a spacer coupled between proximal portions of the inner and outer balloons, at least a portion of the spacer surrounding the adapter.

17. The dual-layer ablation balloon of claim 16, further including a first lumen in fluid communication with the interstitial space and configured and arranged to draw a vacuum within the interstitial space and to draw captured cryogenic fluid out of the interstitial space and into the vacuum lumen.

18. The dual-layer ablation balloon of claim 17, further including a second lumen in fluid communication with the interstitial space and a pressure sensor, the pressure sensor configured and arranged to sense a change in vacuum pressure within the interstitial space associated with a flow of cryogenic fluid through the inner balloon via the second lumen.

19. The dual-layer ablation balloon of claim 16, further including an exhaust lumen in fluid communication with the internal cavity of the inner balloon, the exhaust lumen configured to exhaust the gaseous state cryogenic fluid out of the internal cavity, wherein at least a portion of the length of the exhaust lumen has a clover-leaf-like cross-sectional area.

* * * * *

UNITED STATES PATENT AND TRADEMARK OFFICE
CERTIFICATE OF CORRECTION

| | | |
|---|---|---|
| PATENT NO. | : 11,890,044 B2 | Page 1 of 1 |
| APPLICATION NO. | : 16/467343 | |
| DATED | : February 6, 2024 | |
| INVENTOR(S) | : Tegg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this
First Day of July, 2025

Coke Morgan Stewart
*Acting Director of the United States Patent and Trademark Office*